United States Patent
Au et al.

(10) Patent No.: US 6,286,513 B1
(45) Date of Patent: Sep. 11, 2001

(54) METHODS FOR TREATING SUPERFICIAL BLADDER CARCINOMA

(75) Inventors: Jessie L. S. Au, Columbus, OH (US); M. Guill Wientjes, 2287 Palmleaf Ct., Columbus, OH (US) 43325

(73) Assignees: Jessie L. Au; M. Guill Wientjes, both of Columbus, OH (US)

(*) Notice: Subject to any disclaimer, the term of this patent is extended or adjusted under 35 U.S.C. 154(b) by 0 days.

(21) Appl. No.: 09/177,260

(22) Filed: Oct. 22, 1998

(51) Int. Cl.$^7$ .................................................. A61B 19/00
(52) U.S. Cl. ............................................. 128/898; 604/500
(58) Field of Search ........................... 128/898; 604/500; 525/183, 178

(56) References Cited

U.S. PATENT DOCUMENTS 5,252,673 * 10/1993 Hirano et al. ........................ 525/183
5,301,688 * 4/1994 Stephan et al. ....................... 607/99

OTHER PUBLICATIONS

"Use of pharmacologic data and computer simulations to design an efficacy trial of intravesical mitomycin C therapy for superficial bladder cancer" by Wientjes, et al., *Cancer, Chemotherapy and Pharmacology*, Feb. 17, 1993.

"Apparnt Failure of Current Intravesical Chemotherapy Prophylaxis to Influence the Long–Term Course of Superficial Transitional Cell Carcinoma of the Bladder" by Lamm, et al., *The Journal of Urology*, vol. 153, 1444–1450, May 1995.

Eksborg S, et al. "Intravesical instillation of Adriamycin. A model for standardization of the chemotherapy". *Eur Urol.* 1980;6(4):218–20.

Groos E, et al. "Iintravesical chemotherapy. Studies on the relationship between pH and cytotoxicity". *Cancer*. Sep. 15 1986;58(6):1199–203.

Ilett KF, et al. "Effect of urine pH on the stability of doxorubicin and its recovery from bladder instillations". *Br J Urol*. May 1990;65(5):478–82.

Jauhiainen K, et al. "Optimisimg mitomycin C activity during intravesical instillation". *Urol Res.* 1983;11(2):59–62.

(List continued on next page.)

*Primary Examiner*—David J. Isabella
*Assistant Examiner*—Kelly O'Hara
(74) *Attorney, Agent, or Firm*—Lahive Cockfield, LLP; Peter C. Lauro, Esq.

(57) ABSTRACT

A therapy for preventing tumor recurrence in patients with Ta, T1, and Tis transitional cell carcinoma. The therapy is an adjuvant intravesical therapy, i.e., it is employed on patients following transurethral resection of the Ta, T1, or Tis carcinoma. The therapy comprises the steps of reducing the volume of urine in the bladder of the patient to a value of about 10 ml or less; and then administering an aqueous solution containing at least 2 mg/ml of MMC to the bladder of the patient for a period of at least about 120 minutes. The volume of solution administered to the bladder of the patient is at least about 20 ml. Preferably, the therapy is administered to the patient weekly multiple times. Preferably, the therapy further comprises the step of reducing the amount of urine produced by the patient during the time MMC is administered to the patient to a value of 1 ml/min or less. Preferably, the therapy further comprises the step of administering an alkalinizing agent to the patient before the MMC dosing solution is administered to the patient. The alkalinizing agent is administered in an amount sufficient to increase the pH of the urine produced by the patient during the time of MMC administration to a value of about 6.5 or greater. Preferably, the alkalinizing agent is administered orally.

16 Claims, 12 Drawing Sheets

US 6,286,513 B1
Page 2

OTHER PUBLICATIONS

Lamm DL, et al. "Apparent failure of current intravesical chemotherapy prophylaxis to influence the long–term course of superficial transitional cell carcinoma of the bladder". *J Urol.* May 1995;153(5):1444–50.

Jauhiainen K, et al. "Intravesical cytostatics: pH–dependence of antitumour activity". *Urol Res.* 1985;13(1):19–21.

Rohde D, et al. "7–N–(2–([2–(gamma–L–glutamylamino)–ethyl]–dithio)–ethyl)–mitomycin C (KW–2149) is more active than mitomycin C on chemonaive and drug–resistant urothelial carcinoma cells". *Urol Res.* 1998;26(4):243–7.

Wientjes MG, et al. "Use of pharmacologic data and computer simulations to design an efficacy trial of intravesical mitomycin C therapy for superficial bladder cancer." *Cancer Chemother Pharmacol.* 1993;32(4):255–62.

Yen WC, et al. "Different pH dependency of mitomycin C activity in monolayer and three–dimensional cultures". *Pharm Res.* Dec. 1996;13(12):1887–91.

* cited by examiner

METHODS FOR TREATING SUPERFICIAL BLADDER CARCINOMA

BACKGROUND

Approximately 56,000 new cases of bladder carcinoma are diagnosed each year. Of the newly diagnosed cases, 75–85% are superficial tumors (Ta, T1 and Tis) and 15–25% are invasive tumors (T2–4). The primary treatment for superficial bladder carcinomas is transurethral resection, i.e., surgical removal of the tumor. Unfortunately, tumors recur in 40% to 80% of the patients who undergo transurethral resection. Among the patients with recurrent tumors, 10–20% suffer tumor progression, i.e., muscular invasion or metastasis. Drugs such as methotrexate, doxorubicin, or cisplatin are often administered systemically to patients with invasive or metastatic bladder carcinomas.

Recently, studies have been conducted to determine whether an adjuvant intravesical therapy would be useful for preventing tumor recurrence in patients with superficial bladder carcinomas. Intravesical therapy involves direct administration of a drug into the bladder of the patient following transurethral resection. The goal of adjuvant intravesical therapy is to eliminate the neoplastic and pre-malignant cells that are not removed by surgery.

A few studies have been conducted on the effect of intravesical administration MMC or bacillus Calmette Guerin (BCG). The customary experimental MMC intravesical therapy involved weekly administration of MMC at a dose of 1 mg/ml in 20–40 ml of water for six to eight weeks. These studies have shown that an additional 1–13% of the patients who received the customary experimental MMC intravesical therapy following transurethral resection did not display or have a recurrent tumor at 1 year as compared to patients who undergo transurethral resection alone. Thus, although it was possible to reduce tumor recurrence by the customary experimental MMC intravisical therapy, the improvement was relatively modest.

Accordingly, it is desirable to have a new adjuvant therapy for treating patients with superficial bladder carcinomas.

SUMMARY OF THE INVENTION

A new therapy useful for preventing tumor recurrence in patients with Ta, T1, and Tis transitional cell carcinoma is provided. The new therapy is an adjuvant intravesical therapy, i.e., it is employed on patients following transurethral resection of the Ta, T1, or Tis carcinoma. The new therapy, referred to hereinafter as the "high efficacy therapy" comprises the steps of reducing the volume of urine in the bladder of the patient to a value of about 10 ml or less; and then administering an aqueous solution containing at least 2 mg/ml of MMC to the bladder of the patient for a period of at least about 120 minutes. The volume of solution administered to the bladder of the patient is about 20 ml. Preferably, the high efficacy therapy is administered to the patient weekly for a period of at least six weeks. Preferably, the high efficacy therapy further comprises the step of reducing the amount of urine produced by the patient during the time MMC is administered to the patient to a value of 1 ml/min or less. Preferably, the high efficacy therapy further comprises the step of administering an alkalinizing agent such as, for example, sodium bicarbonate to the patient before the MMC dosing solution is administered to the patient. The alkalinizing agent is administered in an amount sufficient to increase the pH of the urine produced by the patient during the time of MMC administration to a value of about 6.5 or greater. Preferably, the alkalinizing agent is administered orally.

DETAILED DESCRIPTION OF THE INVENTION

Figure 1:
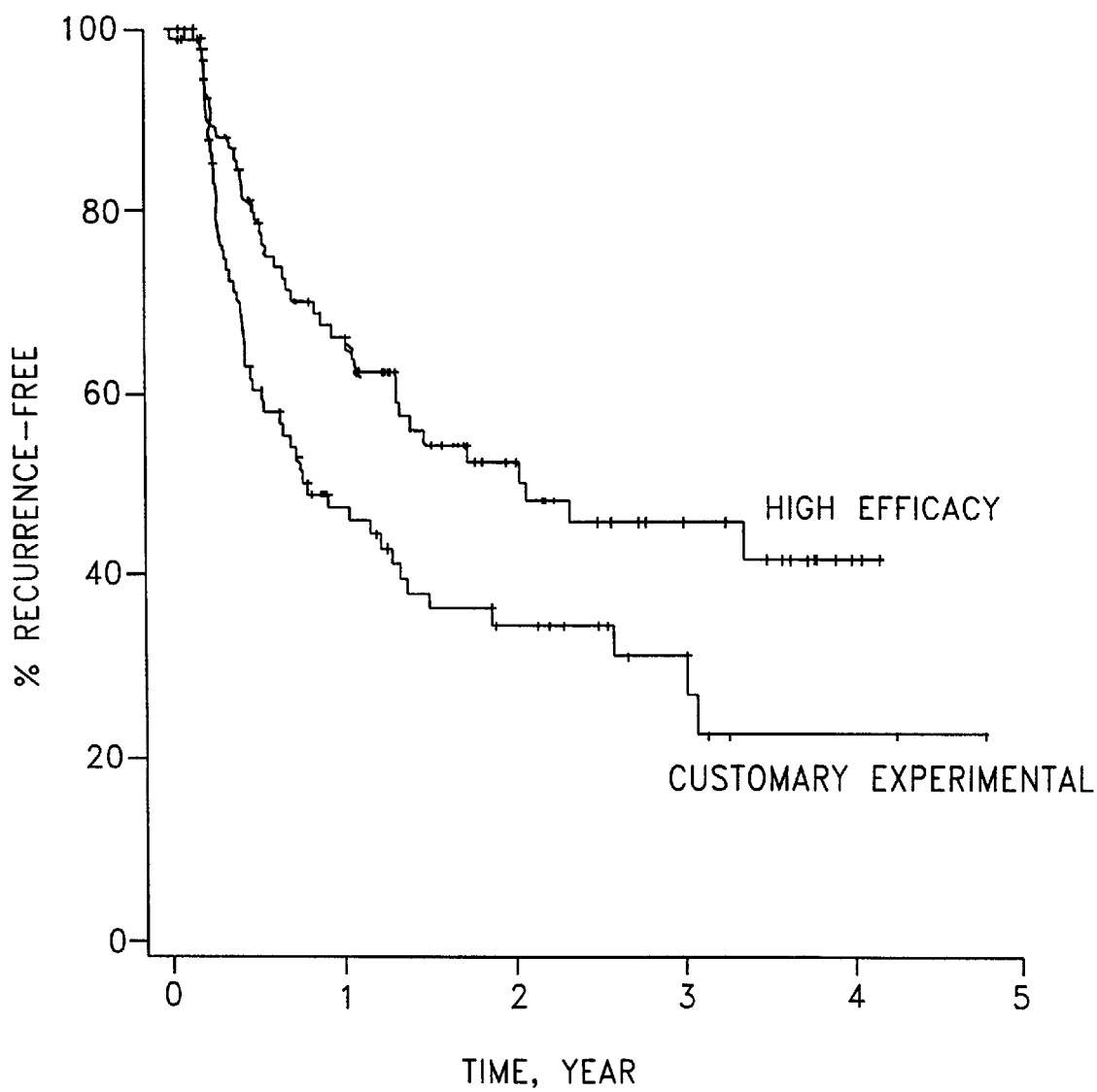
FIG 1. is a Kaplan-Meier curve showing the percentage of patients with Ta, T1 or Tis tumors who are projected to be tumor recurrence free after treatment with the high efficacy therapy as compared to the customary experimental intravesical MMC therapy.
Figure 2:
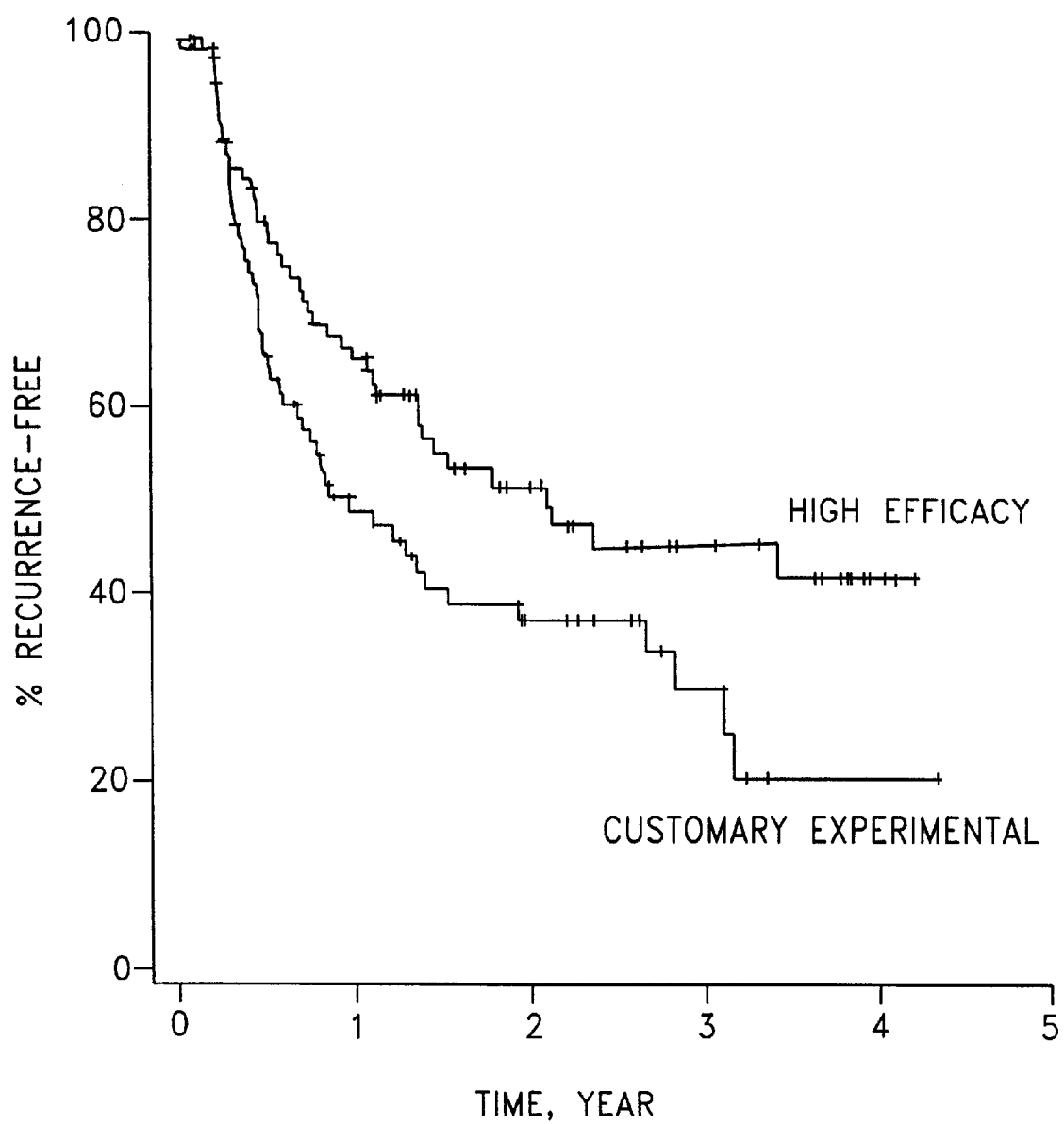
FIG. 2. is a Kaplan-Meier curve showing the percentage of patients with Ta or T1 tumors who are projected to be tumor recurrence free after treatment with the high efficacy therapy as compared to the customary experimental intravesical MMC therapy.
Figure 3:
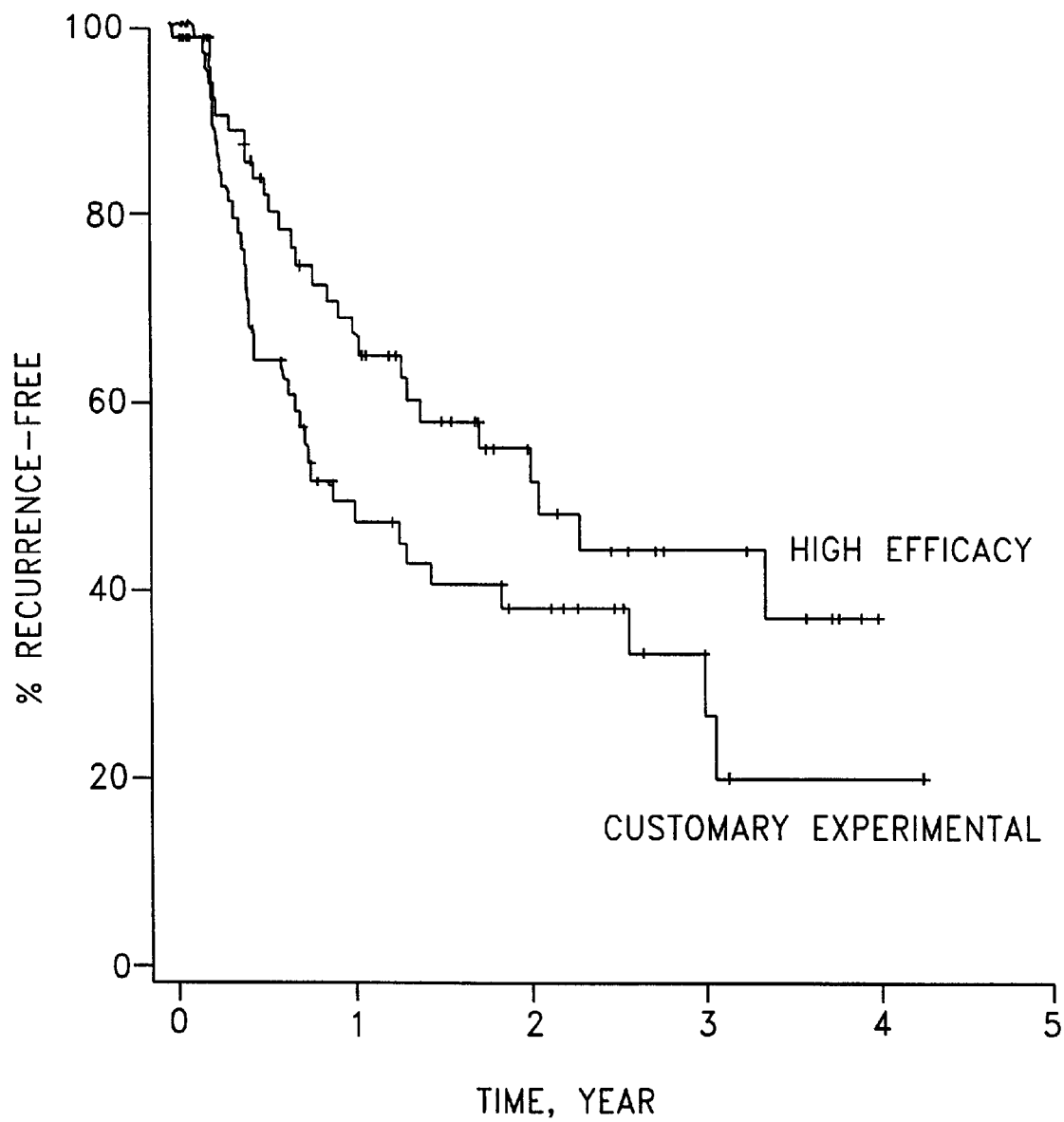
FIG. 3. is a Kaplan-Meier curve showing the percentage of patients with Ta tumors who are projected to be tumor recurrence free after treatment with the high efficacy therapy as compared to the customary experimental intravesical MMC therapy.
Figure 4:
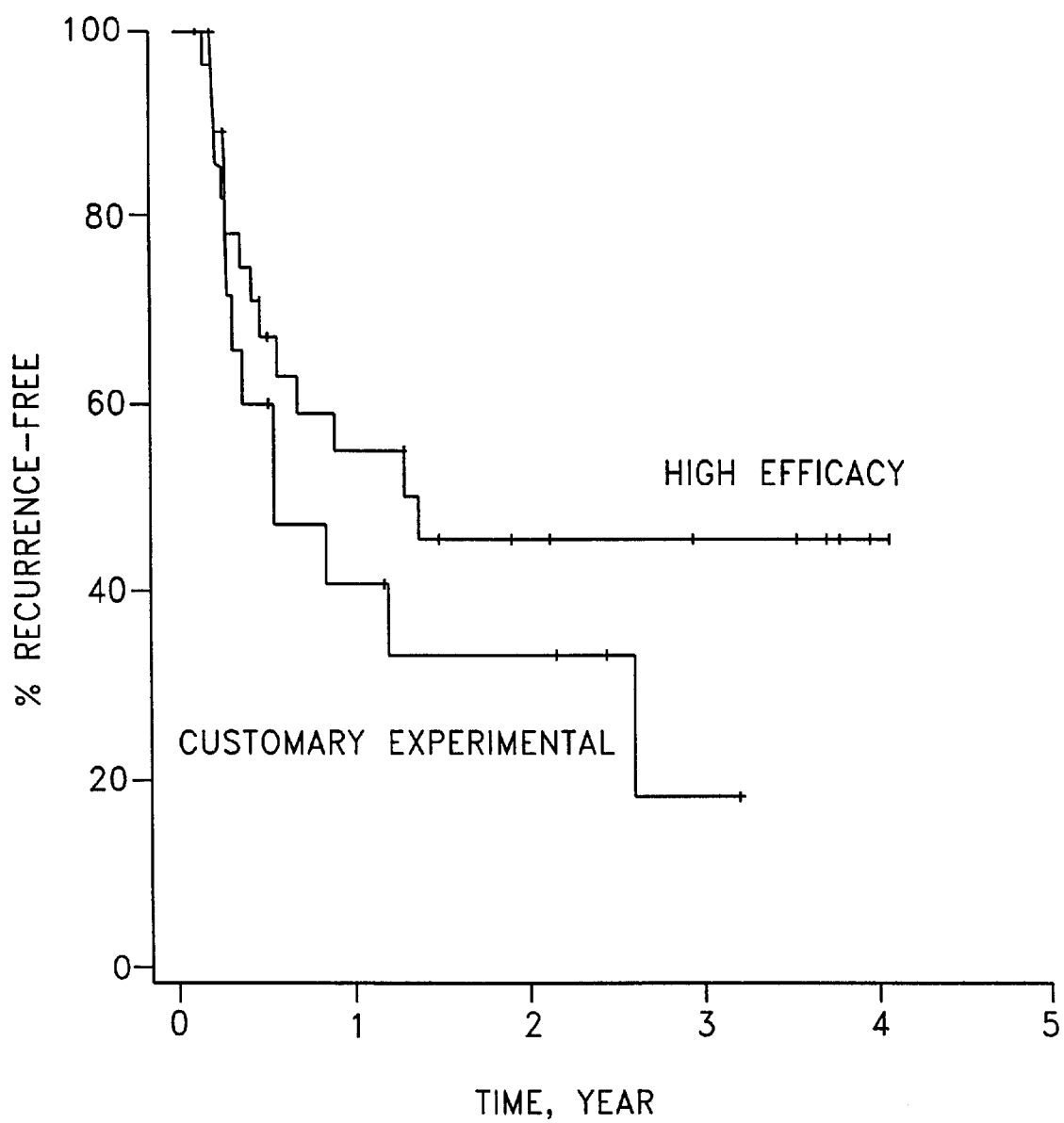
FIG. 4. is a Kaplan-Meier curve showing the percentage of patients with T1 tumors who are projected to be tumor recurrence free after treatment with the high efficacy therapy as compared to the customary experimental intravesical MMC therapy.
Figure 5:
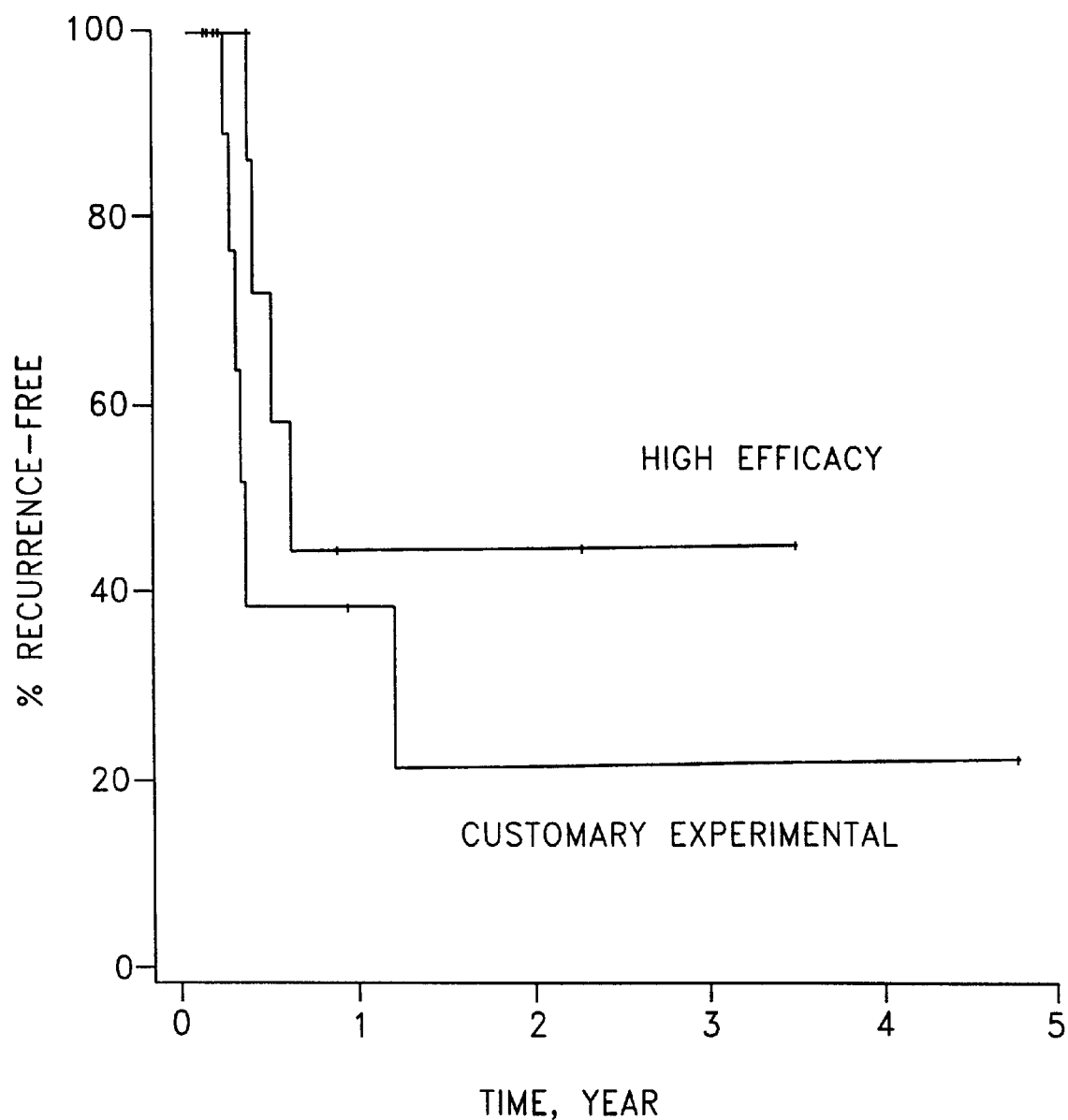
FIG. 5. is a Kaplan-Meier curve showing the percentage of patients with Tis tumors who are projected to be tumor recurrence free after treatment with the high efficacy therapy as compared to the customary experimental intravesical MMC therapy.
Figure 6:
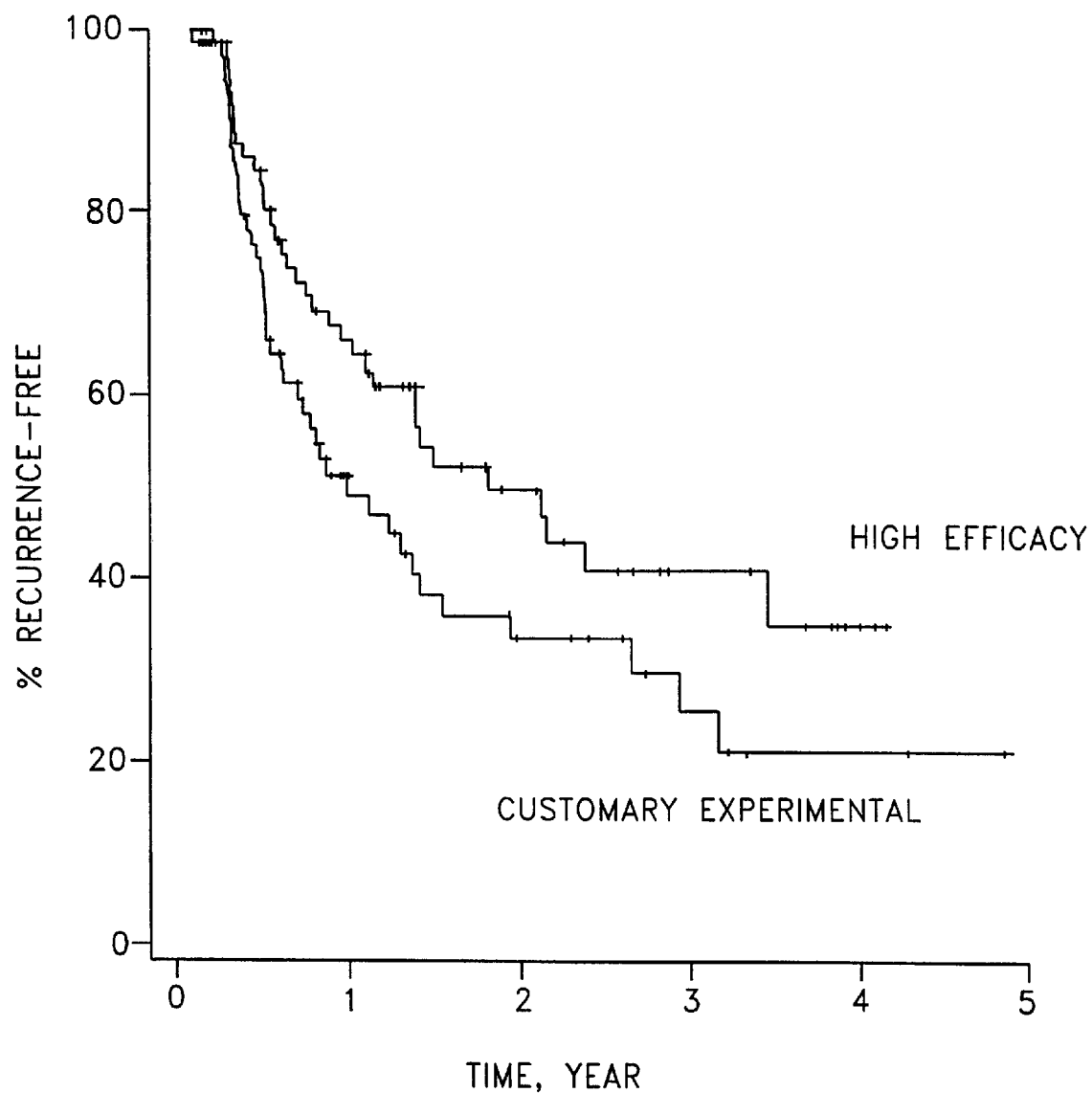
FIG. 6. is a Kaplan-Meier curve showing the percentage of patients with low grade tumors (grade1 and II) who are projected to be tumor recurrence free after treatment with the high efficacy therapy as compared to the customary experimental intravesical MMC therapy.
Figure 7:
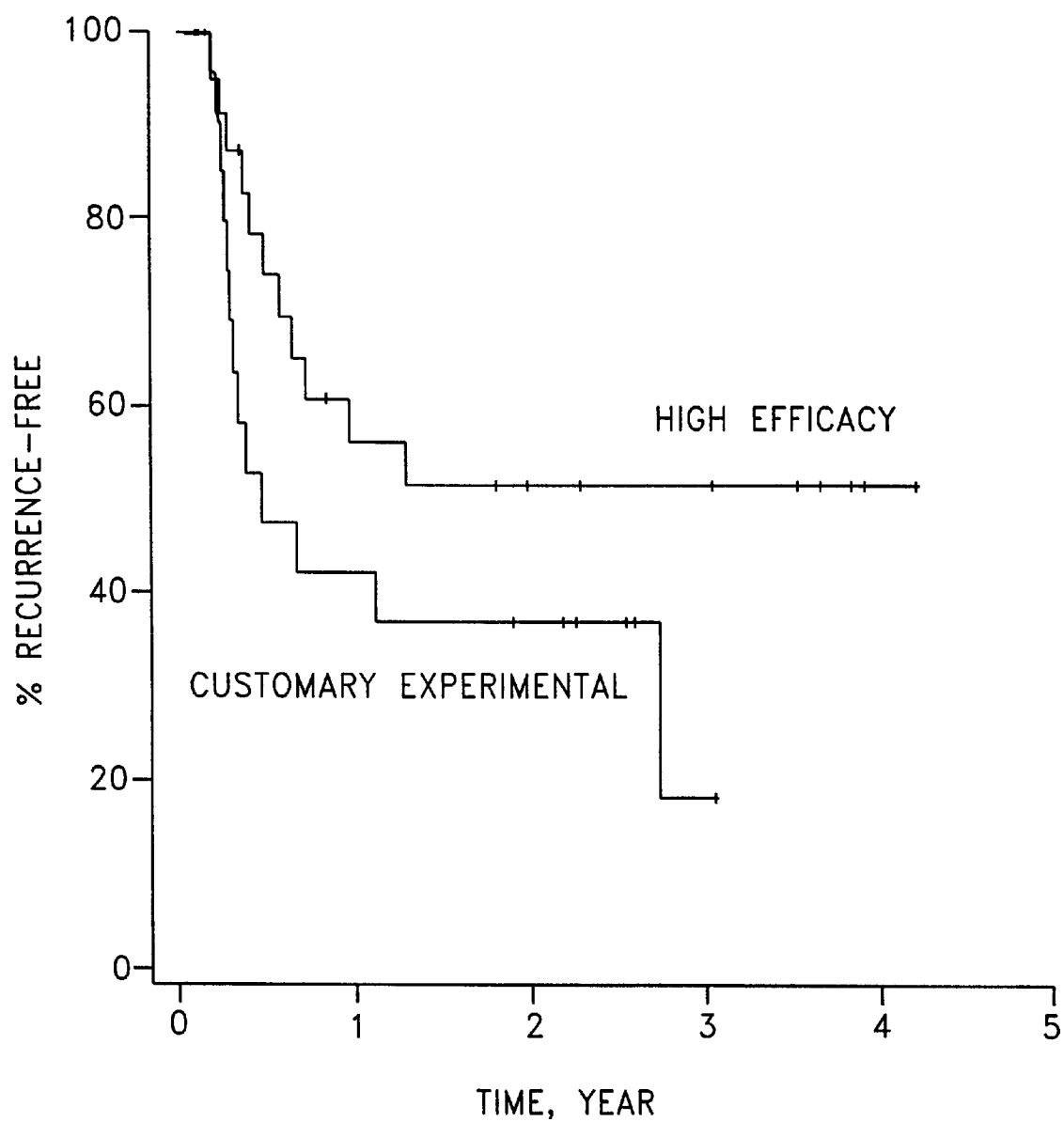
FIG. 7. is a Kaplan-Meier curve showing the percentage of patients with high grade tumors (grade III) who are projected to be tumor recurrence free after treatment with the high efficacy therapy as compared to the customary experimental intravesical MMC therapy.
Figure 8:
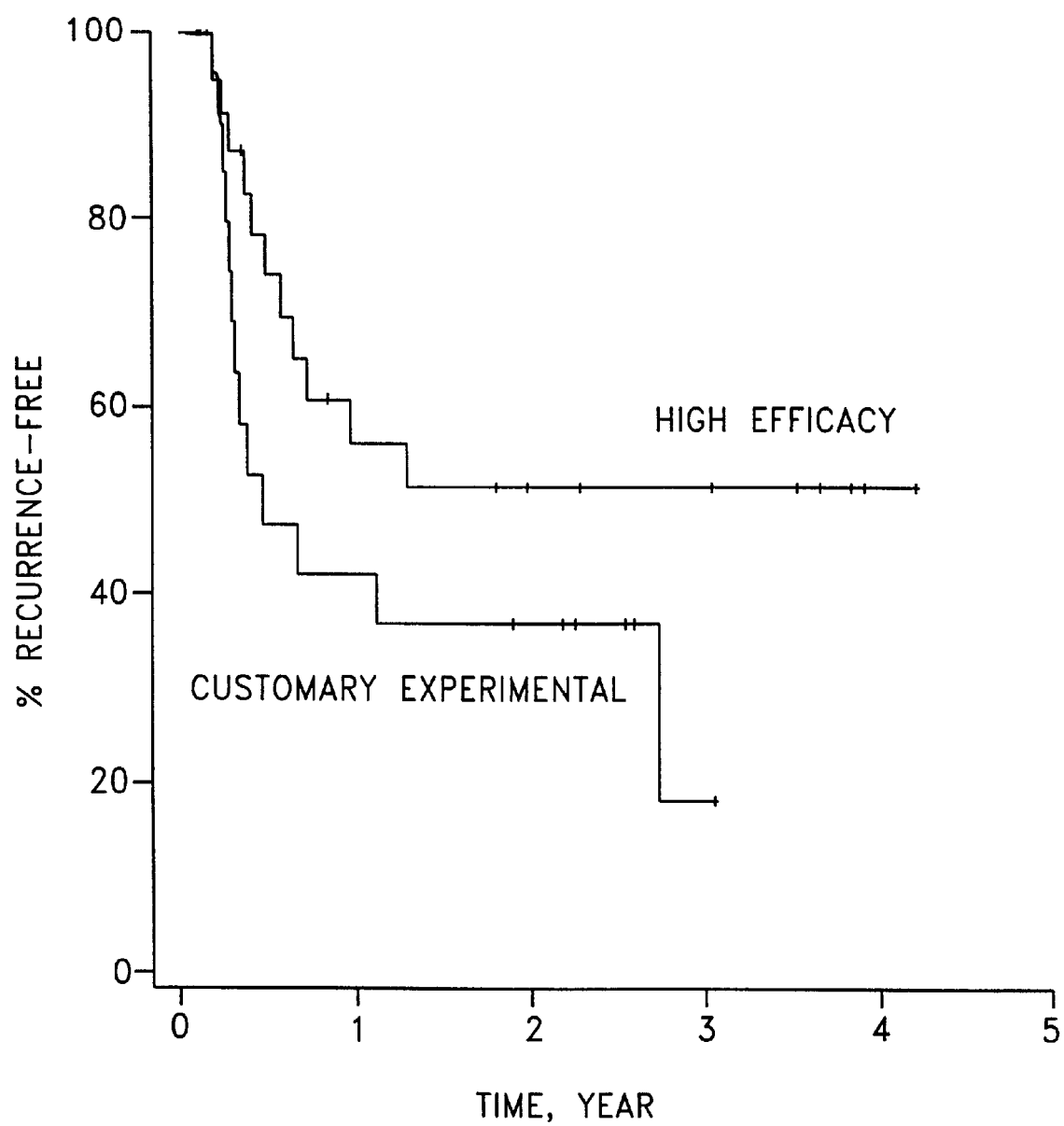
FIG. 8. is a Kaplan-Meier curve showing the percentage of patients with a single (i.e. unifocal) tumor who are projected to be tumor recurrence free after treatment with the high efficacy therapy as compared to the customary experimental intravesical MMC therapy.

A new therapy, referred to herein as a high efficacy therapy, useful for preventing tumor recurrence in patients having superficial transitional cell carcinoma is provided. The high efficacy therapy is an adjuvant therapy which is used in conjunction with transurethral resection of the carcinoma. The high efficacy therapy comprises the steps of (a) reducing the volume of urine in the bladder of the patient to a value of about 10 ml or less and (b) then administering an MMC dosing solution comprising about 18 to 23 ml, preferably about 20 ml of a solution containing at least about 2 mg/ml MMC into the bladder of the patient for a period of at least about 120 minutes. Preferably, the patient receives this therapy weekly multiple times with the first treatment preferably being administered within 4 weeks after surgery.

Prior to administration of the MMC dosing solution, the volume of urine in the bladder in the patient is reduced to about 10 ml or less, preferably to 5 ml or less, more preferably to less than 1 ml. Preferably, the volume of urine is reduced by catherization. Following catherization the patient is preferably instructed to sit up or stand up, and bend forward. Preferably, bladder emptying is confirmed sonographically. If the volume of urine is not sufficiently reduced by the initial emptying, the sequence of standing up and bending forward is repeated until the desired volume is achieved. At times it is useful to instill a small volume of water or physiological saline to dislodge any material blocking the catheter opening.

Then a dosing solution of MMC is instilled into the bladder of the patient. Preferably, the MMC dosing solution is instilled within 5 minutes after emptying of the patient's bladder. The volume of the MMC dosing solution instilled into the patient is about 18–22 ml, preferably about 20 ml. The dosing solution is preferably a sterile aqueous solution which comprises the antibiotic MMC, which may be obtained commercially from Bristol-Myers. The concentration of MMC in the MMC dosing solution is at least about 2 mg/ml of solution. The pH of the MMC dosing solution is preferably from about 6.5 to about 7.5, more preferably about 7. Examples of suitable solvents for use in the dosing solution are sterile water and sterile physiological saline.

The MMC dosing solution is instilled into the patient's bladder using standard equipment and in a conventional manner. Good results have been obtained by inserting a Foley catheter into the bladder through the urethra while the patient lies on his or her back. The MMC dosing solution is dispensed from a sterile container such as, for example, a syringe through the catheter. The catheter is then flushed with just enough air to fill the syringe and to ascertain the delivery of the entire dosing solution. Instillation of excessive air should be avoided. Other similar methods will be equally effective.

The MMC dosing solution is maintained in the bladder for a period of at least about 120 minutes. Preferably, the patient undergoes this therapy weekly multiple times, preferably six times for a total of six treatments. Good results have been achieved by reducing the volume of urine in the patient before treatment to less than 10 ml and by using a 20 ml solution of 40 mg MMC in sterile water, an instillation time of 120 minutes, and six weekly treatments.

Preferably, the high efficacy therapy further comprises reducing urine production in the patient during the time the MMC dosing solution is in the bladder. Preferably, urine production is reduced to a value of less than 1 ml/min or less, more preferably to a value of 0.7 ml/min or less. Urine production is reduced by requesting the patient to avoid or minimize fluid intake for at least 12 hours prior to administration of the MMC solution. Alternatively, urine production is reduced by administering a conventional anti-diuretic to the patient.

Preferably the high efficacy therapy further comprises oral administration of an alkalizing agent, such as for example, sodium bicarbonate to the patient prior to administration of the MMC dosing solution. The alkalinizing agent is administered at a time and in an amount sufficient to maintain the pH of the urine that is produced by the patient during instillation of the MMC dosing solution to a value of about 6.5 or greater. It has been determined that urine pH can be maintained above 6.5 in most individuals by oral administration of about 1.3 g of NaHCO3 at the following three time periods: (a) at bedtime on the night before instillation of the MMC dosing solution, (b) upon rising on the morning of instillation of the MMC dosing solution, and (c) within 2 hours prior to instillation of the MMC dosing solution. If the pH of the urine taken just prior to MMC administration is 6.0 or less, an additional 1.3 g of NaHCO3 can be given, and the MMC instillation delayed for 15 to 30 minutes. In this case the bladder is emptied just prior to instillation of the MMC dosing solution.

Efficacy and Safety

The present high efficacy therapy is useful for delaying or preventing bladder tumor recurrence in patients diagnosed as having superficial transitional cell tumors. Superficial transitional cell tumors fall into three categories: Ta, which is a noninvasive papillary carcinoma; T1 in which the tumor invades the subepithelial connective tissue and is thus located in the lamina propria: and Tis or carcinoma in situ, which is a "flat tumor" in which penetration is limited to the urothelium.

The customary experimental MMC intravesical therapy consists of six weekly treatments with a 20 ml solution containing 1 mg/ml MMC and where no special efforts are made to empty the bladder or to administer the drug within 5 to 15 min after emptying of the bladder. As compared to the customary experimental MMC intravesical therapy, the high efficacy therapy is more effective at reducing the rate of recurrence and increasing the time interval before tumor recurrence is observed in patients diagnosed as having Ta, T1, or Tis carcinoma. The high efficacy therapy is more effective in enhancing the percentage or fraction of Ta, T1, Tis bladder tumor patients that are projected to remain tumor recurrence free for a period of 5 years as compared to the customary experimental MMC intravesical therapy. The high efficacy therapy is more effective than the customary experimental MMC intravesical therapy at delaying and preventing tumor recurrence in patients with multiple tumors. The high efficacy therapy is more effective than the customary experimental MMC intravesical therapy at delaying and preventing tumor recurrence in patients with large tumors, i.e. tumors >5 cm. The high efficacy therapy is more effective than the customary experimental MMC intravesical therapy at delaying and preventing tumor recurrence in patients with aneuploid tumors. The high efficacy therapy is also more effective than the customary experimental MMC intravesical therapy at delaying and preventing tumor recurrence in patients who have developed recurrent tumors despite receiving other adjuvant therapies. Thus, the high efficacy therapy is useful for preventing recurrence in patients who have not responded to other adjuvant therapies such as for example BCG intravesical therapy or the customary experimental MMC intravesical therapy.

It has also been determined that the high efficacy therapy does not elevate levels of MMC in the blood of the patients to a value of greater than about 50 ng/ml. In most instances the high efficacy therapy elevates blood levels of MMC to less than 5 ng/ml. Previous studies have shown that there is no significant host toxicity when patients were given MMC systemically in doses as high as 50 mg and/or when the blood levels of MMC are below 400 ng/ml.

In addition, patients receiving the high efficacy therapy did not exhibit any signs of bone marrow toxicity. A small number of the patients receiving the high efficacy therapy exhibit other toxicities, such as dysuria, cystitis, hematuria, cramps. However, these toxicities were mild. A comparison of the toxicities found in patients receiving the high efficacy therapy and the customary experimental MMC intravesical therapy is shown in Table 1 below.

| Toxicity Comparison | | | |
|---|---|---|---|
| Toxicity | Customary (n = 96) (% of patients) | High efficacy (n = 104) (% of patients) | P |
| Dysuria | 19 | 35 | 0.016 |
| Cystitis | 18 | 24 | 0.166 |
| Leukopenia | 0 | 1 | 1.000 |
| Thrombocytopenia | 0 | 0 | N/A |
| Urinary frequency | 33 | 26 | 0.098 |
| Urgency | 28 | 22 | 0.287 |
| Hematuria | 24 | 26 | 0.946 |
| Pain | 17 | 17 | 0.928 |
| Cramp | 17 | 15 | 0.845 |
| Fever | 5 | 5 | 1.000 |
| Fatigue | 20 | 19 | 0.920 |
| Malaise | 19 | 18 | 0.911 |
| Dermal | 10 | 15 | 0.504 |
| Allergy | 9 | 13 | 0.683 |
| Nausea | 9 | 12 | 0.652 |
| Vomiting | 5 | 4 | 0.740 |
| Any toxicity | 64 | 72 | 0.580 |

The high efficacy therapy produces a higher frequency of dysuria. But this toxicity was mild and did not result in termination of treatment.

EXAMPLE 1

Treatment of Patients with Ta, T1 or Tis Bladder Tumors

One hundred and eight patients with histologically proven primary or recurrent transitional cell carcinoma of grade I to grade III and of stage Ta, T1 or Tis who had their tumors completely resected received the high efficacy therapy within 4 weeks after surgery. The primary solitary tumors were at least 5 cm in diameter, high grade (grade II) or the tumor cells exhibited DNA aneuploidy on image analysis or flow cytometry of the tumor specimen.

The high efficacy therapy was administered once weekly for a total of six treatments. The MMC dosing solution was made by adding 40 mg of MMC to a vial containing 20 ml of sterile water.

To reduce urine production in the patients during treatment with the MMC dosing solution, the patients were instructed to refrain from fluids for 8 hours prior to and during treatment with the MMC dosing solution. To maintain the pH levels of the urine produced during treatment with the MMC dosing solution, the patients were given 1.3 grams of sodium bicarbonate the night prior to treatment, upon rising on the morning of treatment and 30 minutes prior to treatment. Then a Foley catheter was placed in the bladder of the patients and the bladder was drained by gravity. This was accomplished by holding the catheter end below the level of the bladder. The post void residual urine volume was determined using a bladder ultrasound machine. Drainage of the bladder was repeated until the residual urine volume was less than 10 ml. Drainage was aided by having the patient sit up or stand up, or reach forward while standing. Thereafter, 40 mg of MMC in 20 ml sterile water was instilled intravesically by gravity into the bladder of the patient and retained there for 2 hours. After the 2 hour therapy, bladder contents were drained from the patients and the volume and pH of the contents measured.

For purposes of comparison, 97 matching control patients from whom primary Ta, T1 or Tis bladder tumors had been completely resected were subjected to the customary experimental MMC intravesical therapy weekly for six weeks. These patients were not instructed to refrain from fluids for 8 hours prior to or during the customary experimental therapy. Prior to instillation of the 1 mg/ml MMC dosing solution, the patients were placed in the supine or dorsal lithotomy position and a Foley catheter inserted transurethrally into the bladder of the patients. The bladders were drained by gravity and the post void urine residual volume was measured. No attempts were made to further reduce the residual urine volume. Thereafter, 20 mg of MMC in 20 ml sterile water was instilled intravesically by gravity into the bladders of the patients and retained for 2 hours. After the 2 hour therapy, bladder contents were drained from the patients and the volume and pH of the contents measured.

Evaluation

Cytoscopy was performed on each surviving patient quarterly at three months for 2 years and then at 3 months or six months for the remaining 3 years to look for evidence of visible tumors. Urine cytology was performed on each surviving patient quarterly at three months for 2 years and then at 3 months or six months for the remaining 3 years to look for cells with aneuploid DNA contents. Detection of aneuploid cells suggests a recurrent tumor. If necessary, i.e., if tumor recurrence was suspected, the follow-up included biopsy of the suspicious area and transurethral resection of the bladder tumor. Patients with proven recurrence were treated according to standards in the clinical community.

Results

At each time period the number of patients who had developed histologically proven recurrent or progressive disease on biopsy or cytology was determined. The results obtained for each individual patient are shown in Table 2 below. The percentage of patients who remained tumor free at each time period after receiving the high efficacy therapy or the customary experimental therapy is shown in FIG. 1.

As shown in FIG. 1, tumors recurred at a later time in patients receiving the high efficacy treatment than in patients receiving the customary experimental MMC intravesical therapy. The median time to recurrence was 754 days for the patients receiving the high efficacy as compared to 292 days for patients receiving the customary experimental MMC intravesical therapy.

As shown in FIG. 1, the fraction or percentage of patients who are projected to be tumor recurrence-free at the end of 5 years is 41% for the high efficacy treatment versus 20% for the customary experimental MMC intravesical therapy. Thus a patient treated with the high efficacy therapy has a 41% chance of being free of the disease at the end of five years, whereas a patient treated with the customary experimental MMC intravesical therapy had only a 20% chance of being free of the disease recurrence.

TABLE 2

| Patient No. | Customary (C) or High Efficacy (H) Treatment | Date of Administration | Type (Ta, T1, TIS) | Unifocal (U), Multifocal (M) | Previous intravensical therapy | Tumor Recurrence (Y/N/?) | Date of Recurrence |
|---|---|---|---|---|---|---|---|
| 1 | C | 10/07/92 | Ta | M | No | Y | 02/04/94 |
| 2 | C | 10/07/92 | Ta | U | MMC, BCG | N | |
| 3 | C | 06/01/93 | T1 | M | No | Y | 07/19/94 |
| 4 | C | 06/21/93 | T1 | M | Dox, BCG | N | |
| 5 | C | 07/23/93 | TIS | M | Thio, BCG | N | |
| 6 | C | 09/28/93 | Ta | U | Thio | N | |
| 7 | C | 11/18/93 | TIS | M | No | Y | 02/15/94 |
| 8 | C | 11/19/93 | Ta | U | BCG | Y | 04/28/94 |
| 9 | C | 11/24/93 | Ta | U | No | Y | 08/16/94 |
| 10 | C | 11/29/93 | Ta | M | No | Y | 10/13/95 |
| 11 | C | 12/21/93 | Ta | U | No | Y | 09/21/94 |
| 12 | C | 01/04/94 | T1 | U | No | N | |
| 13 | C | 02/15/94 | Ta | M | No | Y | 06/30/94 |
| 14 | C | 02/16/94 | T1 | M | No | N | |
| 15 | C | 02/28/94 | T1 | M | No | Y | 09/16/94 |
| 16 | C | 03/08/94 | Ta | U | No | N | |
| 17 | C | 03/16/94 | Ta | U | No | Y | 07/13/94 |
| 18 | C | 05/04/94 | TIS | U | No | Y | 09/15/95 |
| 19 | C | 05/26/94 | T1 | U | Dox, BCG | Y | 08/30/94 |
| 20 | C | 06/07/94 | T1 | M | No | Y | 11/03/94 |
| 21 | C | 06/24/94 | Ta | M | BCG | Y | 12/02/94 |
| 22 | C | 07/19/94 | Ta | U | Thio, BCG | Y | 01/13/95 |
| 23 | C | 09/07/94 | Ta | U | No | Y | 01/25/95 |
| 24 | C | 09/19/94 | Ta | U | No | Y | 03/13/95 |
| 25 | C | 09/28/94 | T1 | M | No | Y | 04/20/95 |
| 26 | C | 10/19/94 | Ta | U | No | N | |
| 27 | C | 10/21/94 | Ta | U | No | Y | 01/11/95 |
| 28 | C | 11/07/94 | Ta | U | BCG | N | |
| 29 | C | 11/18/94 | Ta | M | Thio, BCG | Y | 05/01/95 |
| 30 | C | 11/23/94 | Ta | M | No | Y | 06/30/97 |
| 31 | C | 11/30/94 | T1 | U | No | Y | 09/30/97 |
| 32 | C | 12/14/94 | Ta | U | Thio, BCG | Y | 11/24/97 |
| 33 | C | 01/04/95 | Ta | U | No | N | |
| 34 | C | 01/12/95 | T1 | M | No | N | |
| 35 | C | 01/17/95 | Ta | M | No | N | |
| 36 | C | 01/18/95 | Ta | M | No | Y | 08/05/96 |
| 37 | C | 02/06/95 | Ta | U | BCG | Y | 01/04/96 |
| 38 | C | 02/15/95 | Ta | U | Thio, BCG | Y | 03/26/98 |
| 39 | C | 02/16/95 | Ta | U | Thio | Y | 05/02/95 |
| 40 | C | 02/20/95 | Ta | M | BCG | Y | 07/20/95 |
| 41 | C | 03/14/95 | Ta | U | No | Y | 07/08/96 |
| 42 | C | 03/21/95 | Ta | U | MMC | N | |
| 43 | C | 04/13/95 | Ta | M | Thio, BCG | N | |
| 44 | C | 05/01/95 | Ta | U | No | N | |
| 45 | C | 05/10/95 | Ta | M | No | N | |
| 46 | C | 05/11/95 | Ta | M | BCG | Y | 07/17/95 |
| 47 | C | 07/05/95 | T1 | M | No | Y | 10/04/95 |
| 48 | C | 07/25/95 | Ta | U | No | N | |
| 49 | C | 08/10/95 | TIS | M | BCG, Brop, Reg | Y | 10/26/95 |
| 50 | C | 08/16/95 | TIS | M | ? | Y | 11/12/95 |
| 51 | C | 11/21/95 | Ta | U | No | Y | 07/12/96 |
| 52 | C | 11/22/95 | Ta | M | MMC | Y | 04/11/96 |
| 53 | C | 11/30/95 | T1 | M | No | Y | 03/20/96 |
| 54 | C | 12/01/95 | Ta | U | BCG | Y | 02/19/96 |
| 55 | C | 03/05/96 | Ta | M | Thio, BCG | Y | 05/22/96 |
| 56 | C | 03/06/96 | Ta | U | Thio | N | |
| 57 | C | 03/11/96 | T1 | M | Thio | N | |
| 58 | C | 03/25/96 | Ta | U | BCG | N | |
| 59 | C | 05/16/96 | T1 | M | BCG | Y | 08/07/96 |
| 60 | C | 05/31/96 | Ta | U | No | N | |
| 61 | C | 06/27/96 | Ta | M | BCG | N | |
| 62 | C | 07/12/96 | TIS | M | BCG, Reg | Y | 09/18/96 |
| 63 | C | 07/19/96 | Ta | M | No | Y | 09/16/97 |
| 64 | C | 07/19/96 | Ta | M | BCG | Y | 10/08/96 |
| 65 | C | 07/31/96 | Ta | M | No | Y | 04/22/97 |
| 66 | C | 08/21/96 | Ta | M | No | Y | 05/26/97 |
| 67 | C | 09/25/96 | Ta | M | BCG | N | |
| 68 | C | 10/08/96 | Ta | U | No | N | |
| 69 | C | 10/16/96 | Ta | U | Thio, BCG | N | |
| 70 | C | 10/17/96 | Ta | M | No | Y | 01/24/97 |
| 71 | C | 10/17/96 | TIS | M | No | Y | 01/28/97 |
| 72 | C | 10/25/96 | T1 | M | BCG | Y | 01/12/98 |
| 73 | C | 12/03/96 | Ta | U | No | N | |

TABLE 2-continued

| Patient No. | Customary (C) or High Efficacy (H) Treatment | Date of Administration | Type (Ta, T1, TIS) | Unifocal (U), Multifocal (M) | Previous intravensical therapy | Tumor Recurrence (Y/N/?) | Date of Recurrence |
|---|---|---|---|---|---|---|---|
| 74 | C | 12/12/96 | Ta | M | No | Y | 09/09/97 |
| 75 | C | 12/16/96 | T1 | U | No | Y | 04/15/97 |
| 76 | C | 12/20/96 | Ta | M | No | Y | 03/27/97 |
| 77 | C | 01/07/97 | Ta | U | No | Y | 08/21/97 |
| 78 | C | 01/22/97 | Ta | M | BCG | N | |
| 79 | C | 02/12/97 | T1 | U | No | N | |
| 80 | C | 02/26/97 | Ta | M | No | N | |
| 81 | C | 03/12/97 | Ta | M | No | Y | 05/08/97 |
| 82 | C | 05/13/97 | Ta | U | BCG | N | |
| 83 | C | 06/20/97 | TIS | M | No | N | |
| 84 | C | 09/18/97 | T1 | U | No | Y | 12/02/97 |
| 85 | C | 10/03/97 | TIS | M | No | N | |
| 86 | C | 10/03/97 | TIS | U | No | N | |
| 87 | C | 11/26/97 | Ta | U | No | N | |
| 88 | C | 01/07/98 | Ta | M | No | N | |
| 89 | C | 02/05/98 | TIS | U | No | N | |
| 90 | C | 02/11/98 | Ta | U | No | N | |
| 91 | C | 02/19/98 | TIS | M | Reg | N | |
| 92 | C | 02/24/98 | T1 | M | No | N | |
| 93 | C | 03/04/98 | Ta | M | No | Y | 06/01/98 |
| 94 | C | 03/11/98 | Ta | M | No | N | |
| 95 | C | 04/02/98 | Ta | U | No | Y | 06/02/98 |
| 96 | H | 10/07/92 | TIS | M | No | Y | 02/08/93 |
| 97 | H | 01/13/93 | Ta | U | MMC, Thio, BCG | N | |
| 98 | H | 02/24/93 | T1 | U | BCG | N | |
| 99 | H | 04/13/93 | Ta | M | MMC,BCG | N | |
| 100 | H | 04/22/93 | T1 | M | Thio, BCG | N | |
| 101 | H | 05/18/93 | T1 | U | No | Y | 08/17/93 |
| 102 | H | 10/21/93 | Ta | M | ? | Y | 03/18/94 |
| 103 | H | 11/24/93 | T1 | U | No | N | |
| 104 | H | 12/06/93 | T1 | U | No | N | |
| 105 | H | 12/16/93 | TIS | M | BCG | N | |
| 106 | H | 12/22/93 | TIS | M | BCG | N | |
| 107 | H | 12/22/93 | Ta | M | No | Y | 01/08/96 |
| 108 | H | 12/29/93 | Ta | U | No | N | |
| 109 | H | 01/12/94 | T1 | M | BCG | Y | 10/03/94 |
| 110 | H | 01/26/94 | T1 | M | No | N | |
| 111 | H | 02/10/94 | T1 | M | No | Y | 09/23/94 |
| 112 | H | 02/16/94 | Ta | U | MMC, Thio, BCG | Y | 07/13/94 |
| 113 | H | 02/16/94 | Ta | M | Intron A, BCG | Y | 10/26/94 |
| 114 | H | 02/24/94 | Ta | M | MMC, Thio | Y | 11/15/95 |
| 115 | H | 03/30/94 | T1 | U | No | N | |
| 116 | H | 04/06/94 | T1 | U | No | N | |
| 117 | H | 05/23/94 | Ta | U | No | N | |
| 118 | H | 06/08/94 | TIS | M | No | Y | 01/03/95 |
| 119 | H | 06/09/94 | Ta | U | Dox | N | |
| 120 | H | 06/27/94 | Ta | U | Thio, BCG | Y | 12/15/95 |
| 121 | H | 07/06/94 | T1 | M | No | Y | 12/05/95 |
| 122 | H | 07/13/94 | Ta | M | No | N | |
| 123 | H | 07/13/94 | T1 | M | No | Y | 10/04/94 |
| 124 | H | 07/14/94 | T1 | M | No | Y | 11/08/95 |
| 125 | H | 08/09/94 | Ta | U | Thio | N | |
| 126 | H | 08/18/94 | Ta | U | Intron A | Y | 09/11/95 |
| 127 | H | 08/29/94 | Ta | M | Thio | Y | 02/05/98 |
| 128 | H | 09120/94 | Ta | U | BCG | Y | 09/30/96 |
| 129 | H | 10/05/94 | Ta | M | No | N | |
| 130 | H | 11/25/94 | Ta | M | No | Y | 04/23/97 |
| 131 | H | 12/09/94 | Ta | U | No | Y | 02/19/95 |
| 132 | H | 01/04/95 | T1 | U | No | N | |
| 133 | H | 02/01/95 | TIS | M | No | Y | 07/25/95 |
| 134 | H | 03/08/95 | Ta | M | BCG | Y | 05/23/95 |
| 135 | H | 03/10/95 | Ta | M | No | Y | 06/05/95 |
| 136 | H | 03/17/95 | Ta | M | MMC, BCG | Y | 05/29/95 |
| 137 | H | 03/30/95 | Ta | U | No | N | |
| 138 | H | 04/10/95 | Ta | M | BCG | N | |
| 139 | H | 04/11/95 | T1 | U | No | Y | 10/04/95 |
| 140 | H | 05/03/95 | T1 | M | BCG | Y | 07/18/95 |
| 141 | H | 05/24/95 | Ta | M | No | N | |
| 142 | H | 05/26/95 | Ta | M | BCG | Y | 12/14/95 |
| 143 | H | 10/17/95 | Ta | U | MMC, BCG | N | |
| 144 | H | 11/15/95 | T1 | U | No | Y | 11/28/96 |

TABLE 2-continued

| Patient No. | Customary (C) or High Efficacy (H) Treatment | Date of Administration | Type (Ta, T1, TIS) | Unifocal (U), Multifocal (M) | Previous intravensical therapy | Tumor Recurrence (Y/N/?) | Date of Recurrence |
|---|---|---|---|---|---|---|---|
| 145 | H | 11/22/95 | TIS | M | No | N | |
| 146 | H | 11/29/95 | T1 | M | No | N | |
| 147 | H | 12/06/95 | Ta | M | No | N | |
| 148 | H | 12/14/95 | Ta | M | No | Y | 04/10/97 |
| 149 | H | 12/20/95 | Ta | M | No | Y | 09/05/96 |
| 150 | H | 01/03/96 | Ta | M | No | N | |
| 151 | H | 01/11/96 | T1 | U | No | N | |
| 152 | H | 01/17/96 | Ta | M | No | N | |
| 153 | H | 02/21/96 | Ta | M | No | N | |
| 154 | H | 03/01/96 | Ta | U | BCG | Y | 08/26/96 |
| 155 | H | 03/04/96 | Ta | M | BCG | N | |
| 156 | H | 03/06/96 | Ta | M | No | Y | 06/24/97 |
| 157 | H | 03/12/96 | Ta | U | No | N | |
| 158 | H | 03/19/96 | Ta | U | BCG | Y | 08/23/96 |
| 159 | H | 03/19/96 | TIS | M | No | N | |
| 160 | H | 03/21/96 | Ta | M | No | Y | 02/10/97 |
| 161 | H | 04/02/96 | TIS | M | No | Y | 08/07/96 |
| 162 | H | 04/12/96 | Ta | U | BCG | N | |
| 163 | H | 04/26/96 | Ta | U | BCG | N | |
| 164 | H | 06/04/96 | Ta | M | Thio, BCG | N | |
| 165 | H | 07/03/96 | Ta | M | No | Y | 02/14/97 |
| 166 | H | 07/24/96 | Ta | M | No | N | |
| 167 | H | 08/09/96 | Ta | M | BCG | N | |
| 168 | H | 08/20/96 | Ta | U | BCG | N | |
| 169 | H | 08/26/96 | Ta | M | BCG | N | |
| 170 | H | 10/11/96 | Ta | U | No | Y | 10/06/97 |
| 171 | H | 10/31/96 | T1 | M | BCG | N | |
| 172 | H | 11/19/96 | Ta | U | No | N | |
| 173 | H | 12/10/96 | Ta | U | Thio, BCG | Y | 03/04/97 |
| 174 | H | 12/13/96 | T1 | U | No | Y | 05/12/97 |
| 175 | H | 12/13/96 | T1 | U | BCG | Recurrence | |
| 176 | H | 01/08/97 | Ta | M | No | Y | 07/31/97 |
| 177 | H | 01/22/97 | T1 | U | No | Y | 05/07/97 |
| 178 | H | 02/14/97 | Ta | M | No | N | |
| 179 | H | 03/03/97 | Ta | U | MVAC* | ? | |
| 180 | H | 03/27/97 | Ta | U | No | N | |
| 181 | H | 04/02/97 | Ta | U | No | N | |
| 182 | H | 04/03/97 | Ta | U | No | N | |
| 183 | H | 04/25/97 | T1 | M | BCG | Y | 09/23/97 |
| 184 | H | 04/29/97 | Ta | M | No | Y | 04/24/98 |
| 185 | H | 05/30/97 | Ta | M | BCG | N | |
| 186 | H | 07/30/97 | Ta | U | No | N | |
| 187 | H | 08/06/97 | Ta | M | No | Y | 06/04/98 |
| 188 | H | 09/04/97 | T1 | M | No | Y | 11/12/97 |
| 189 | H | 10/01/97 | Ta | M | No | N | |
| 190 | H | 10/16/97 | Ta | U | ? | N | |
| 191 | H | 10/16/97 | T1 | M | No | Y | 01/13/98 |
| 192 | H | 11/13/97 | Ta | M | No | N | |
| 193 | H | 11/27/97 | Ta | M | No | N | |
| 194 | H | 11/27/97 | TIS | M | Reg | N | |
| 195 | H | 12/11/97 | Ta | M | No | N | |
| 196 | H | 01/14/98 | T1 | M | No | N | |
| 197 | H | 02/12/98 | TIS | M | BCG | N | |
| 198 | H | 02/12/98 | Ta | U | No | N | |
| 199 | H | 02/28/98 | Ta | M | No | N | |
| 200 | H | 03/24/98 | Ta | U | ? | N | |
| 201 | H | 05/27/98 | T1 | M | ? | N | |

Abbreviations of drugs given intravesically
Thio: thiotepa
Dox: doxorubicin
Brop: bropiramine
Reg: regressin
MMC and BCG: as defined in text
MVAC: methotrexate, vinblastine, doxorubicin, cisplatin, given by intravenous infusion

EXAMPLE 2

Treatment of Patients with Recurrent Ta or T1 Tumors

Seventy-seven patients from whom recurrent Ta, T1 or Tis tumors had been resected were treated weekly for six weeks with the high efficacy therapy as described above in example 1 and 68 patients from whom recurrent Ta, T1 or Tis tumors had been resected were treated by the customary experimental therapy as described in example 1. All patients had undergone at least one previous round of therapy, to several previous rounds of resection plus chemotherapy consisting of treatment with BCG, MMC, doxorubicin and doxorubicin and cisplatin. For example, 44 patients treated with the high efficacy treatment and 42 patients treated with the customary experimental method had at least two tumor resections. Thirty-eight patients in each of the two treatment arms fad received previous tumor resections plus at least one series of adjuvant chemotherapy. All patients were evaluated as described in example 1. The results are shown in Table 2 and FIG. 12.

Figure 12:
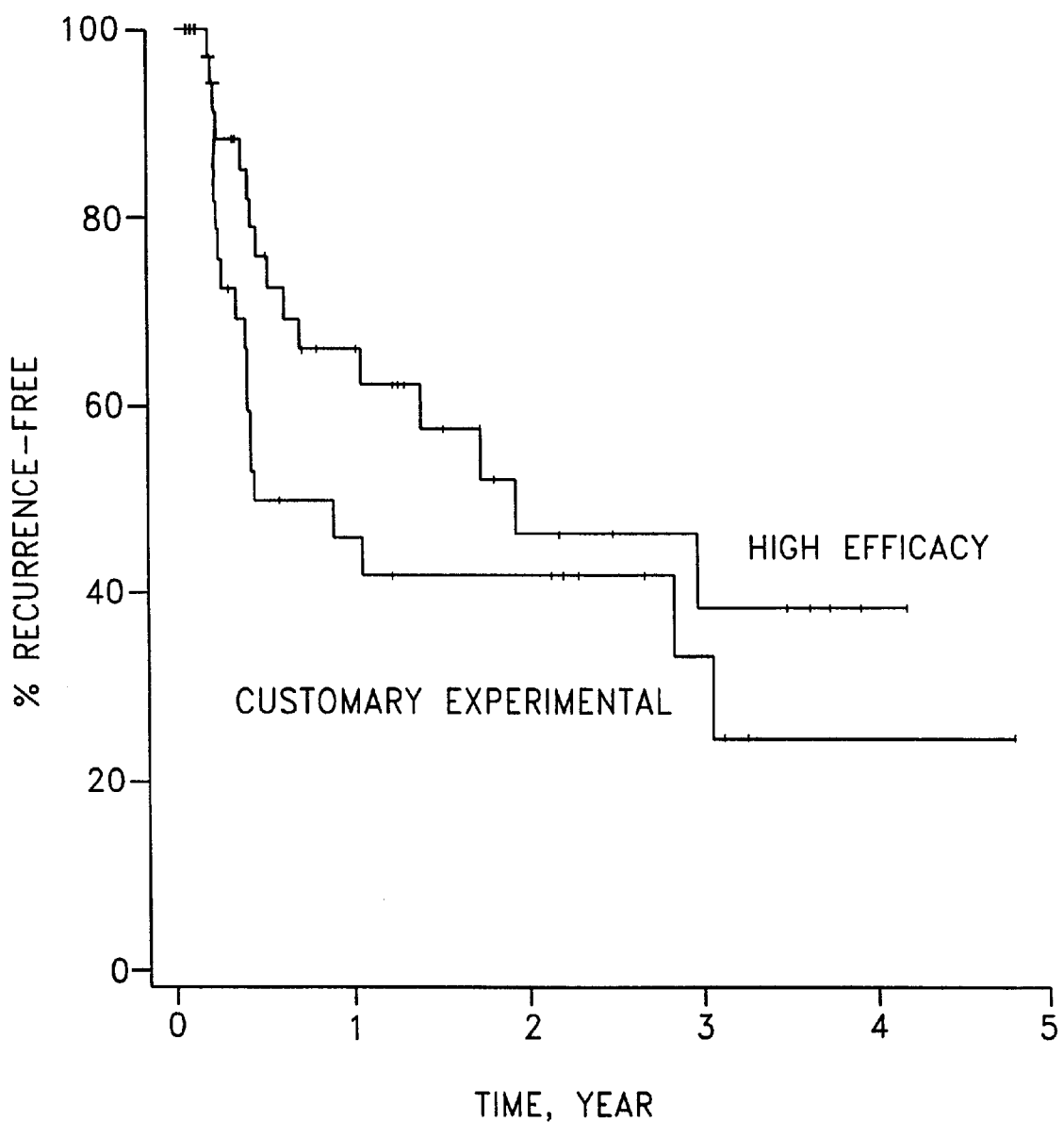
FIG. 12. is a Kaplan-Meier curve showing the percentage of patients who with recurrent tumors and one or more previous intravesical drug or BCG therapies and who are projected to be tumor recurrence free after treatment with the high efficacy therapy as compared to the customary experimental intravesical MMC therapy.

As shown in FIG. 12, the median time to recurrence was 754 days for patients treated by the high efficacy therapy versus 339 days for patients treated by the customary experimental therapy. The projected 5-year tumor recurrence free rate is 39% for patients receiving the high efficacy therapy and 26% for patients receiving the customary experimental therapy.

EXAMPLE 3

Treatment of Patients with Multifocal Ta, T1, Tis Tumors

Sixty-five of patients from whom 3 or more Ta, T1,or Tis tumors had been removed were treated weekly for six weeks with the high efficacy therapy as described above in example 1 and 52 patients from whom 3 or more Ta, T1, or Tis tumors had been removed were treated weekly for six weeks with standard MMC intravsical therapy as described in example 1. All patients received the follow-up described in example 1. The results are shown in Table 2 and FIG. 9.

Figure 9:
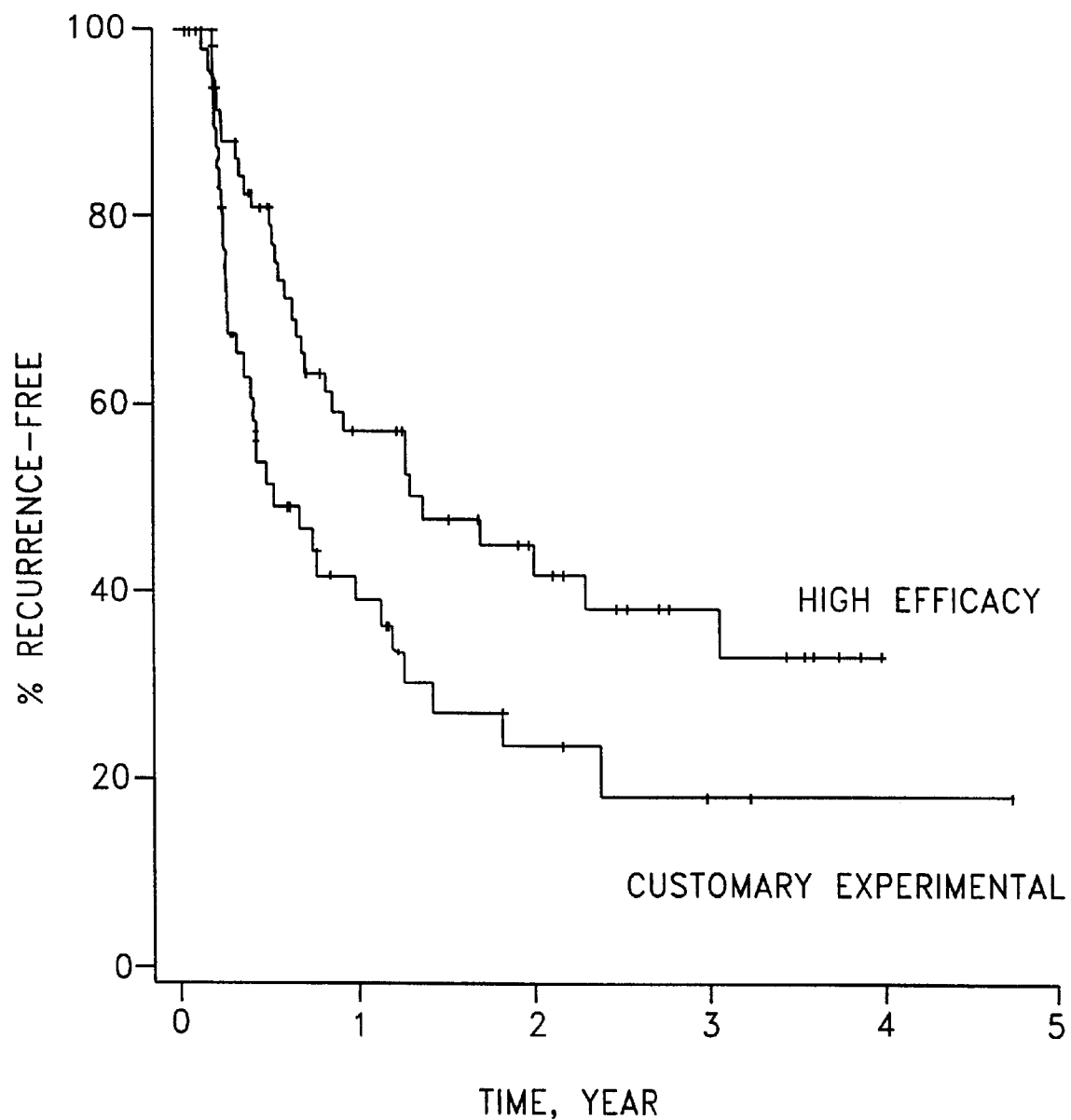
FIG. 9. is a Kaplan-Meier curve showing the percentage of patients with multiple (i.e., multifocal) tumors who are projected to be tumor recurrence free after treatment with the high efficacy therapy as compared to the customary experimental intravesical MMC therapy.
Figure 10:
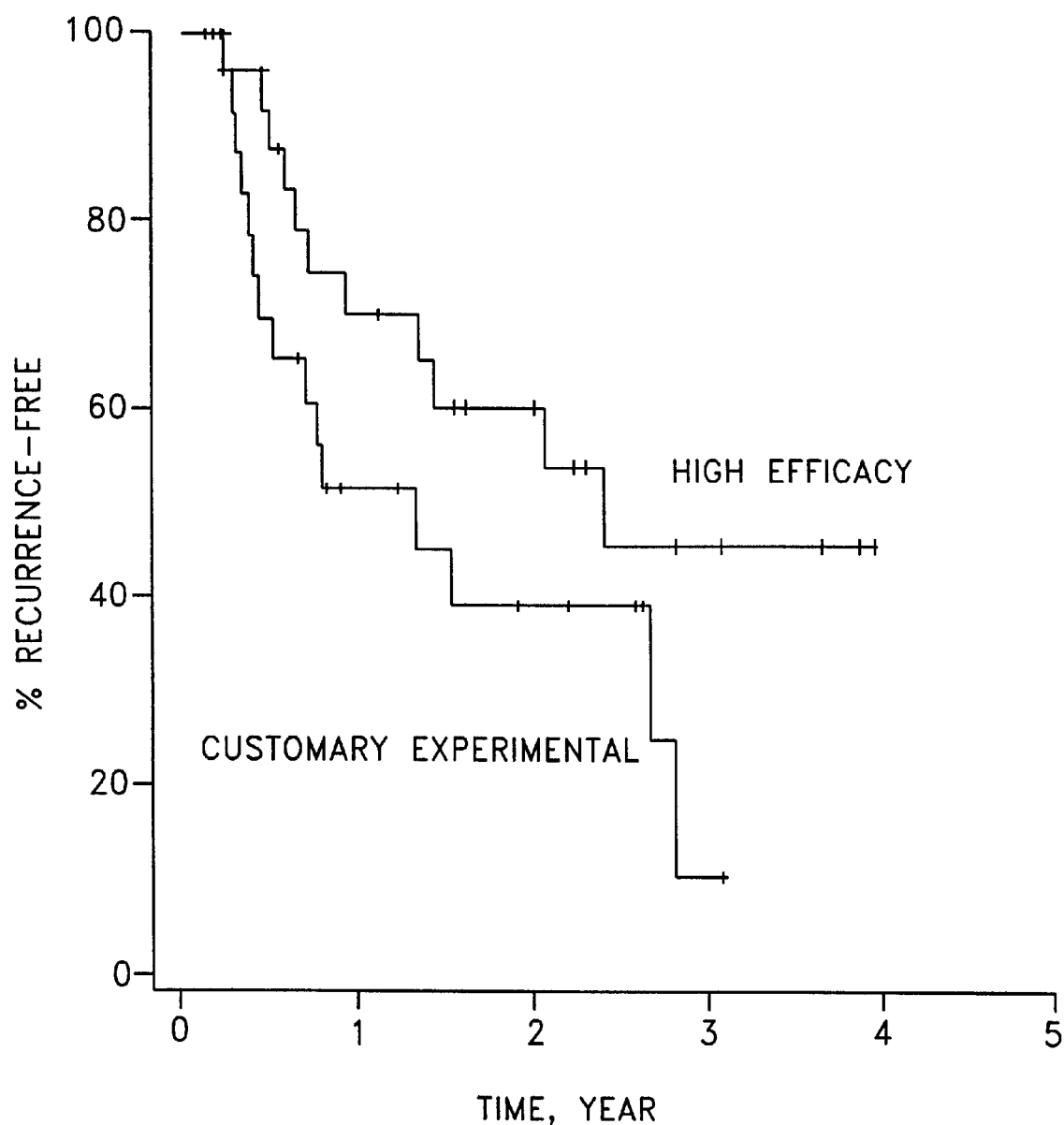
FIG. 10. is a Kaplan-Meier curve showing the percentage of patients with newly-diagnosed (i.e.) primary tumors who are projected to be tumor recurrence free after treatment with the high efficacy therapy as compared to the customary experimental intravesical MMC therapy.
Figure 11:
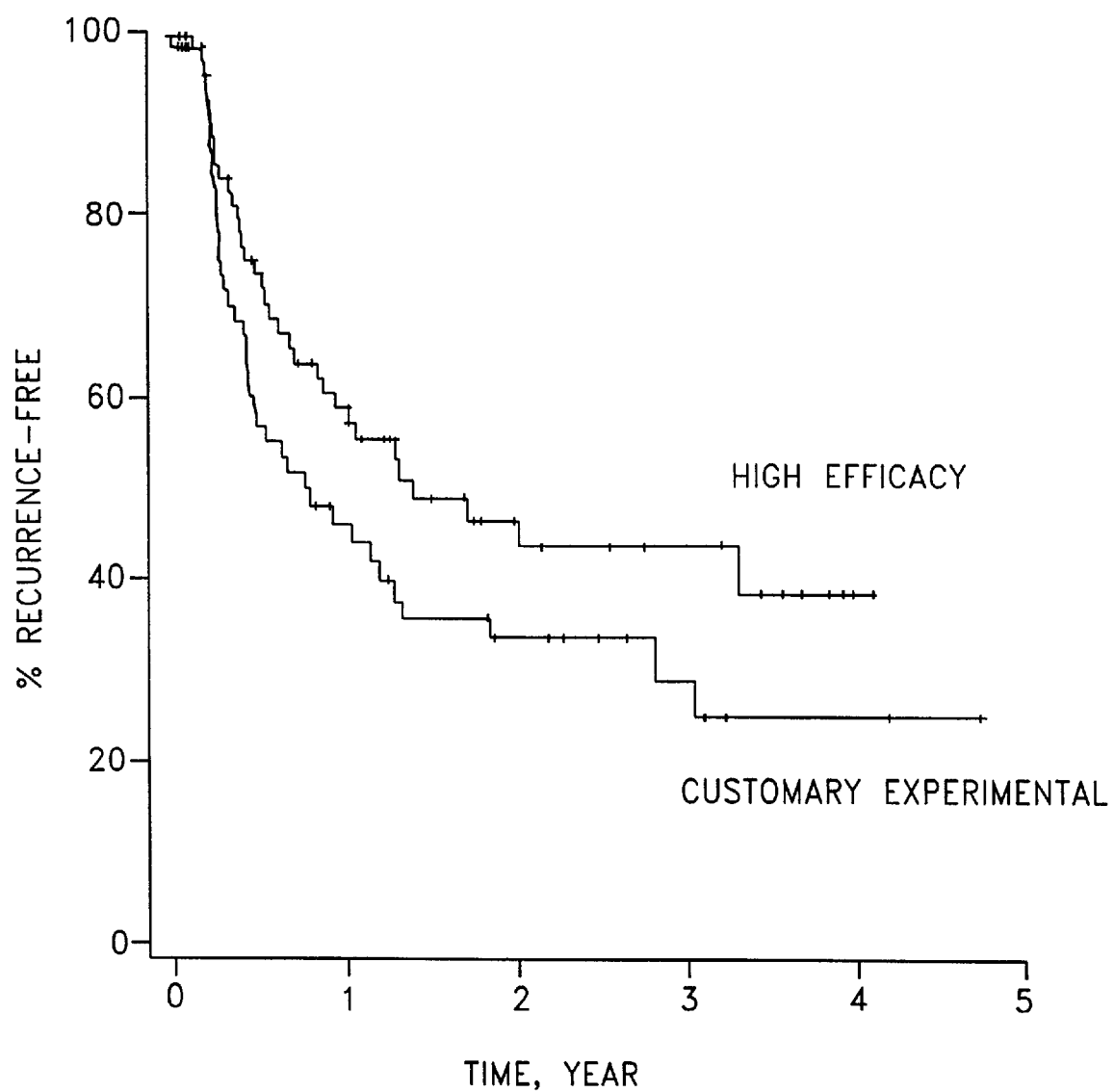
FIG. 11. is a Kaplan-Meier curve showing the percentage of patients with recurrent tumors, i.e., the patients underwent more than one transurethral resection, who are projected to be tumor recurrence free after treatment with the high efficacy therapy as compared to the customary experimental intravesical MMC therapy.

As shown in FIG. 9, the median time to tumor recurrence was 488 days by the standard treatment. The projected 5-year recurrence free rate is 32% for patients receiving the high efficacy therapy and 17% for patients receiving the customary experimental therapy.

EXAMPLE 4

Treatment of Patients with Tis Tumors

Ten patients from whom one or more foci of Tis had been removed were treated weekly for six weeks with the high efficacy therapy as described above in example 1 and 12 patients from whom one or more foci of Tis had been removed were treated weekly for six with the standard MMC intravesical therapy as described in example 1. All patients treated by the high efficacy treatment versus 106 days for patients treated by the customary experimental treatment. The projected 5-year recurrence free rate is 43% for the high efficacy treatment and 19% for the standard treatment.

EXAMPLE 5

Treatment of Patients with Low Grade Tumors

Eighty-one patients from whom low grade tumors (i.e., grade I and grade II) had been removed were treated weekly for six weeks with the high efficacy therapy as described above in example 1 and 64 patients from whom low grade tumors were had been removed were treated weekly for six weeks with the customary experimental therapy as described in example 1. All patients were evaluated as described in example 1. The median time to recurrence was 637 days for patients treated by the high efficacy treatment versus 339 days for patients treated by the customary experimental treatment. The projected 5-year recurrence free value is 35% for the high efficacy treatment and 21% for the customary experimental treatment.

EXAMPLE 6

Treatment of Patients with High Grade Tumors

Twenty-seven patients from whom high grade tumors (i.e., grade III) had been removed were treated weekly for six weeks with the high efficacy therapy as described above in example 1 and 23 patients from whom high grade tumors had been removed were treated weekly for six weeks with the customary experimental therapy as described in example 1. All patients were evaluated as described in example 1. The median time to recurrence was not reached for patients treated by the high efficacy treatment versus 179 days for patients treated by the customary experimental treatment. The projected 5-year recurrence free value is 52% for the patients receiving the high efficacy treatment and 19% for the customary experimental treatment.

Overall Bladder Wall Exposure to MMC

A commonly used measure of drug exposure for anticancer agent is the product of exposure concentration and duration, or AUC (area under the curve). Based on previous in vitro results which have shown that for MMC, the drug concentration is more important than treatment duration, we have modified the measure of exposure. i.e. the time integral of concentration to the power of 1.24, so that the measure of exposure is represented by the equation $C^n \times T$ where C represents concentration. T represents time of exposure, and 1.24. The drug exposure in the urinary bladder can be determined from the drug concentration in the urine and can serve as a measure of exposure to the tumor tissue. The urinary AUC, $C^n \times T$, urinary production and pH, observed in a random group of patients receiving the high efficacy therapy or the conventional experimental therapy, is shown in table 3 below. A p value lower than 0.05 indicates that the difference is statistically significant.

TABLE 3

| | Customary experimental therapy Mean ± standard deviation | High efficacy therapy Mean + standard deviation | P value |
|---|---|---|---|
| Urinary AUC, mg. min/ml | 24.2 ± 14.7 | 57.6 + 37.2 | 0.0001 |
| Urinary $C^n \times T$ $mg^n$. min/ml | 97.2 ± 77.08 | 291 ± 283 | 0.0001 |
| Urine production, ml/min | 1.23 ± 0.86 | 1.05 ± 0.74 | 0.048 |
| pH | 6.13 ± 0.84 | 6.80 ± 0.81 | 0.0001 |

As shown in the Table 3, the average drug exposure in the group of patients receiving the high efficacy therapy, when measured as AUC and $C^n \times T$, is 2 and 2.4 times the exposure in the group of patients receiving the customary experimental therapy.

The Kaplan-Meier Curve is a conventional tool used to project treatment outcome such as the % of patients who remain alive or free of disease at a certain time interval. (Martin Bland, Introduction to Medical Statistics (1994) Oxford Press). The Kaplan Meier Curve was used to compare the customary experimental therapy to the high efficacy therapy. When compared to the customary experimental therapy, the high efficacy therapy increased the percentage of all patients who are projected to remain recurrence-free for longer than 5 years from 20 to 41%. The improvement was similar for patients with T1 tumors which were growing in the deeper bladder tissue layers (i.e. increase from 16% to 44%) and for patients with Ta tumors which were growing in the urothelial surface of the bladder (i.e. increase from 20% to 37%).

These results are surprising in view of predictions that have been made regarding treatment efficacy in patients treated with different intravesical therapies. It has been predicted that an 8.4 fold improvement in $C^n \times T$ over the customary experimental therapy would be needed in order to achieve a 20% increase in the fraction or percentage of patients that remained free of tumors at one year as compared to control patients that receive no adjuvant intravesical therapy. It has also been predicted that a 3-fold increase in $C^n \times T$ would benefit only patients with Ta tumors, would not benefit patients with T1 tumors and would produce only an 8% improvement in the percentage of patients who are projected to remain free of tumors at one year.

What is claimed is:

1. A method for treating superficial bladder carcinoma comprising:
   (b) providing a patient who has undergone transurethral resection of a superficial bladder carcinoma;
   (b) reducing the volume of urine in said patient to a value of 10 ml or less; and
   (c) instilling a dosing solution of from about 18 to 22 ml into the bladder of said patient over a period of at least about 120 min, said dosing solution comprising at least 2 mg/ml mitomycin C.

2. The method of claim 1 further comprising reducing the urine output of the patient during instillation of the dosing solution to a value of about 1 ml/min.

3. The method of claim 2 further comprising maintaining the pH of the urine produced by said patient during instillation of the dosing solution to a value of about 6.5 or greater.

4. The method of claim 1 further comprising maintaining the pH of the urine produced by said patient during instillation of the dosing solution to a value of about 6.5 or greater.

5. The method of claim 1 wherein the volume of urine in said patient is reduced to a value of less than 5 ml.

6. The method of claim 1 wherein the volume of urine in said patient is reduced to a value of less than 2 ml.

7. The method of claim 1 wherein the pH of the dosing solution is about 7.

8. The method of claim 1 wherein step (b) and step (c) are repeated multiple times on a weekly basis.

9. The method of claim 8 wherein step (b) and step (c) are repeated for at least six weeks.

10. The method of claim 1 wherein said patient has undergone transurethral resection of a Ta tumor.

11. The method of claim 1 wherein said patient has undergone transurethral resection of a T1 tumor.

12. The method of claim 1 wherein said patient has undergone transurethral resection of a Tis tumor.

13. The method of claim 1 wherein said patient has had recurrent tumors and has undergone more than one transurethral resection.

14. The method of claim 1 wherein step (b) and step (c) are performed within 6 weeks after the patient has undergone transurethral resection of a superficial bladder carcinoma.

15. The method of claim 1 wherein said dosing solution is a sterile aqueous solution.

16. The method of claim 1 wherein the dosing solution has a volume of about 20 ml.

* * * * *